(12) United States Patent
Hodges

(10) Patent No.: US 6,823,750 B2
(45) Date of Patent: Nov. 30, 2004

(54) METHOD OF PREVENTING SHORT SAMPLING OF A CAPILLARY OR WICKING FILL DEVICE

(75) Inventor: Alastair McIndoe Hodges, San Diego, CA (US)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 10/408,836

(22) Filed: Apr. 4, 2003

(65) Prior Publication Data

US 2004/0040394 A1 Mar. 4, 2004

Related U.S. Application Data

(63) Continuation of application No. 09/536,234, filed on Mar. 27, 2000, now Pat. No. 6,571,651.

(51) Int. Cl.[7] ................... G01N 10/00; G01N 33/487
(52) U.S. Cl. ........................... 73/864.72; 422/69
(58) Field of Search ................... 73/864.83–864.85, 73/864.01–864.02, 864.72, 863, 864.91, 64.56, 864.81, 864.51; 422/55–58, 68.1, 101–102, 50, 69; 204/403, 556; 436/180; 435/14; 600/584

(56) References Cited

U.S. PATENT DOCUMENTS

| | | |
|---|---|---|
| 3,129,146 A | 4/1964 | Hassler |
| 3,527,251 A | 9/1970 | Hagstrom et al. |
| 4,053,381 A | 10/1977 | Hamblen et al. |
| 4,233,029 A | 11/1980 | Columbus |
| 4,254,083 A | 3/1981 | Columbus |
| 4,301,412 A | 11/1981 | Hill et al. |
| 4,301,414 A | 11/1981 | Hill et al. |
| 4,303,887 A | 12/1981 | Hill et al. |
| 4,308,028 A | 12/1981 | Elkins |
| 4,605,629 A | 8/1986 | Lange et al. |
| 4,654,197 A | 3/1987 | Lilja et al. |
| 4,738,827 A | 4/1988 | Pierotti |
| 4,774,192 A | 9/1988 | Terminello et al. |
| 4,790,979 A | 12/1988 | Terminello et al. |
| 4,832,914 A | 5/1989 | Tam et al. |
| 4,898,231 A | 2/1990 | Miyazaki |
| 4,900,424 A | 2/1990 | Birth et al. |
| 4,983,416 A | 1/1991 | Hunsinger et al. |
| 5,019,351 A | 5/1991 | Schulz |
| 5,120,420 A | 6/1992 | Nankai et al. |
| 5,126,034 A | 6/1992 | Carter et al. |
| 5,128,015 A | 7/1992 | Szuminsky et al. |
| 5,135,719 A | 8/1992 | Hillman et al. |
| 5,141,868 A | 8/1992 | Shanks et al. |
| 5,178,831 A | 1/1993 | Sakota et al. |

(List continued on next page.)

FOREIGN PATENT DOCUMENTS

| | | |
|---|---|---|
| AU | A-54873/94 | 2/1997 |
| CA | 1190839 | 7/1985 |
| DE | 19747 875 A1 | 5/1999 |

(List continued on next page.)

OTHER PUBLICATIONS

Derwent–Acc–No.: 1982–KG826 E abstract of SU 873115B Alckhin et al "Automatic Sample Feeders for Mass Analyser–Uses Rotating Cassette with Capillary Dispersing Elements", Oct. 1981.

(List continued on next page.)

*Primary Examiner*—Thomas P. Noland
(74) *Attorney, Agent, or Firm*—McClennen & Fish LLP

(57) ABSTRACT

The current invention provides a device, and a method for using the device, for ensuring that a capillary or wicking fill device is fully filled. In particular this invention is directed to, but not limited to, use with capillary or wicking action filled electrochemical sensors suitable for use in analyzing blood or interstitial fluids.

30 Claims, 2 Drawing Sheets

U.S. PATENT DOCUMENTS

| | | | |
|---|---|---|---|
| 5,192,415 A | 3/1993 | Yoshioka et al. |
| 5,225,163 A | 7/1993 | Andrews |
| 5,229,282 A | 7/1993 | Yoshioka et al. |
| 5,306,623 A | 4/1994 | Kiser et al. |
| 5,320,732 A | 6/1994 | Nankai et al. |
| 5,346,672 A | 9/1994 | Stapleton et al. |
| 5,351,563 A | 10/1994 | Karpf et al. |
| 5,382,346 A | 1/1995 | Uenoyama et al. |
| 5,384,028 A | 1/1995 | Ito |
| 5,384,091 A | 1/1995 | Golz et al. |
| 5,385,846 A | 1/1995 | Kuhn et al. |
| 5,413,690 A | 5/1995 | Kost et al. |
| 5,418,142 A | 5/1995 | Kiser et al. |
| 5,437,999 A | 8/1995 | Diebold et al. |
| 5,445,967 A | 8/1995 | Deuter |
| 5,508,171 A | 4/1996 | Walling et al. |
| 5,509,410 A | 4/1996 | Hill et al. |
| 5,628,890 A | 5/1997 | Carter et al. |
| 5,635,358 A | 6/1997 | Wilding et al. |
| 5,645,709 A | 7/1997 | Birch et al. |
| 5,707,799 A | 1/1998 | Hansmann et al. |
| 5,731,212 A | 3/1998 | Gavin et al. |
| 5,814,522 A | 9/1998 | Zimmer et al. |
| 5,922,604 A | 7/1999 | Stapleton et al. |
| 5,942,102 A | 8/1999 | Hodges et al. |
| 5,997,817 A | 12/1999 | Crismore et al. |
| 6,090,251 A | 7/2000 | Sundberg et al. |
| 6,153,147 A | 11/2000 | Craig |
| 6,605,475 B1 | 8/2003 | Taylor et al. |
| 6,612,111 B1 | 9/2003 | Hodges et al. |
| 2003/0167862 A1 * | 9/2003 | Hodges | 73/864.72 |
| 2004/0096358 A1 * | 5/2004 | Blankenstein et al. | 422/58 |

FOREIGN PATENT DOCUMENTS

| | | |
|---|---|---|
| EP | 0 255 291 A1 | 2/1988 |
| EP | 0 303 784 A | 2/1989 |
| EP | 0 345 781 A2 | 12/1989 |
| EP | 0 351 892 A2 | 1/1990 |
| EP | 0 170 375 B1 | 5/1990 |
| EP | 0 443231 A | 8/1991 |
| EP | 0 451 981 A2 | 10/1991 |
| EP | 483117 A2 | 4/1992 |
| EP | 0 560 336 A1 | 9/1993 |
| EP | 608006 A2 | 7/1994 |
| EP | 0 620 437 A | 10/1994 |
| GB | 2 186 078 A | 8/1987 |
| WO | WO 89/08713 | 9/1989 |
| WO | WO 93/20932 | 10/1993 |
| WO | WO 94/29712 | 12/1994 |
| WO | WO 95/16198 | 6/1995 |
| WO | WO 95/17966 | 7/1995 |
| WO | WO 95/28634 | 10/1995 |
| WO | WO 97/18464 | 5/1997 |
| WO | WO 98/43074 | 10/1998 |
| WO | WO 01/72220 | 10/2001 |

OTHER PUBLICATIONS

Derwent–Acc–No.: 1987–042058, abstract of SU 1239552 A Bulgakov et al "Viscosity meter for oil industry—has pressure sensor connected via follower with shift connected to sample Chamber", Jun. 1986.

Abstract; "Electrochemical Measuring System with Multi-zone Sensors"; EP0609760; Published Mar. 7, 1995.

PCT Int. Search Report, dated May 7, 2002. PCT Int. App. No. PCT/US01/09675.

EP Communication pursuant to Article 96(2) EPC dated Sep. 23, 2003, App. 01 922 698.4–1234, LifeScan, Inc.

* cited by examiner

METHOD OF PREVENTING SHORT SAMPLING OF A CAPILLARY OR WICKING FILL DEVICE

RELATED APPLICATION

This application is a continuation of application Ser. No. 09/536,234, filed Mar. 27, 2000, now U.S. Pat. No. 6,571,651.

FIELD OF THE INVENTION

The present invention relates to a device and method for use in the sampling and analyzing of bodily fluids, such as blood or interstitial fluid, which prevents short sampling.

BACKGROUND OF THE INVENTION

The management of many medical conditions requires the measurement and monitoring of a variety of analytes, e.g., glucose, in bodily fluids. Currently, the measurement of analytes in blood typically requires a venipuncture or finger puncture to obtain blood for sampling purposes. More recently, techniques for analyzing interstitial fluid components have been developed. Regardless of the bodily fluid tested or analytical method used, it is important that sufficient sample is collected in order to ensure adequate test results. In prior art methods, however, adequate sample collection is often a matter of trial and error.

It is therefore desirable to have a sampling and analyzing device giving a clear signal that adequate sample has been collected before the sampling device, e.g., a needle or other penetration device, is removed from the patient's body. It is also desirable that such a device be suitable for hospital bedside and home use.

Capillary and wicking fill devices are well-known as sampling devices and as sensing devices. However, one of the deficiencies of the prior art is that there is either no cue, or only a user-reliant visual cue, to indicate whether the device is fully filled.

SUMMARY OF THE INVENTION

The present invention provides a device, and a method for making and using the device, for ensuring that a capillary or wicking fill device is fully filled. In particular, the invention is directed to, but not limited to, use with capillary or wicking action-filled electrochemical sensors.

In one embodiment of the present invention, a device for sampling a fluid is provided, the device including a pre-chamber having an interior surface and a first volume, the pre-chamber being capable of exerting a first capillary force, the device further including a sensing chamber in fluid communication with the pre-chamber, the sensing chamber having an interior surface and a second volume, the sensing chamber being capable of exerting a second capillary force, wherein the first volume is not less than the second volume, and wherein a differential exists between the capillary forces, the differential being sufficient to cause flow of fluid from the pre-chamber to substantially fill the sensing chamber. The differential in capillary forces can result from the first and second pre-chamber walls being spaced apart at distance greater than the distance between the first and second sensing chamber walls. The differential can also result from the surface roughness, defined as the actual surface area divided by the geometric surface area, of the pre-chamber being less than that of the sensing chamber. Use of one or more surface treatments, which can be the same or different, in one or both of the pre-chamber and sensing chamber can result in a differential capillary force. The surface treatment can include, for example, a hydrophilic or hydrophobic substance. Surface treatments can be selected from surfactants, block copolymers, hygroscopic compounds, ionizable substances, and mixtures thereof.

In a further embodiment, one or both chambers can include, for example, one or more materials which contribute to the capillary force, such as meshes, fibrous materials, porous materials, powders, and mixtures or combinations thereof. Where a mesh is used, a smaller mesh can be used in the pre-chamber than that used in the analysis chamber. The mesh can be made of polyolefin, polyester, nylon, cellulose, polystyrene, polycarbonate, polysulfone or mixtures thereof. Fibrous filling material such as polyolefin, polyester, nylon, cellulose, polystyrene, polycarbonate, and polysulfone, or other nonwoven or melt blown polymers can be used. The porous material can include, for example, a sintered powder or a macroporous membrane, the membrane including polysulfone, polyvinylidenedifluoride, nylon, cellulose acetate, polymethacrylate, polyacrylate, or mixtures thereof. The powder, which can be soluble or insoluble in the sample, can include, for example, microcrystalline cellulose, soluble salts, insoluble salts, and sucrose.

In a further embodiment, the device includes electrodes capable of use in an electrochemical cell, or a detector capable of detecting a condition wherein the pre-chamber contains a volume of fluid sufficient to substantially fill the sensing chamber. A glucose monitoring test strip can include the device.

In yet another embodiment of the present invention, a method is provided for ensuring that a sensing device is substantially filled with a sample of fluid including: providing a device as described above; contacting the device with the fluid for a sufficient period of time to allow the fluid to enter the pre-chamber in an volume equal to or greater than the volume of the sensing chamber; and allowing the sample to flow from the pre-chamber to the sensing chamber, such that the sensing chamber is substantially filled. The method can further include the step of determining presence or absence of an analyte in the sample, e.g., conducting a quantitative measurement or electrochemical measurement of the analyte. The analyte can include, for example, a substance such as glucose, lactate, cholesterol, enzymes, nucleic acids, lipids, polysaccharides, and metabolites. The sample can include, for example, a biological fluid, such as a body fluid of an animal or plant, e.g., interstitial fluid, blood, tears, expectorate, saliva, urine, semen, vomitus, sputum, fruit juice, vegetable juice, plant sap, nectar, and biological fluid-based food products. Non-biological fluids that can be tested include non-biological fluid-based food products or beverages, drinking water, process water, and water-based solutions.

In a further embodiment of the present invention, a method of manufacturing a device as described above is provided, the method including: forming an aperture extending through a sheet of electrically resistive material, the aperture defining a side wall of the sensing chamber; mounting a first thin layer to a first side of the sheet and extending over the aperture whereby to define a first sensing chamber end wall; mounting a second thin layer to a second side of the sheet and extending over the aperture whereby to define a second sensing chamber end wall in substantial overlying registration with the first thin layer, whereby the sheet and layers form a strip; removing a section of the strip which overlaps the sensing chamber and an edge of the strip whereby to define a notch; mounting a first covering layer to a first side of the strip and extending over the notch whereby to define a first pre-chamber wall; and mounting a second covering layer to a second side of the strip and extending over the notch whereby to define a second pre-chamber wall in substantial overlying registration with the first covering layer.

In a further embodiment, the first and second thin layers can include a first and second electrode layer, the electrode layers facing in towards the cell. The electrodes, which can substantially cover the aperture, which can be circular, can include, for example, a noble metal, e.g., palladium, platinum, and silver, optionally sputter coated. An adhesive can be used to adhere the electrode layers to the sheet, e.g., a heat activated adhesive.

In a further embodiment, the chamber contains a chemical for use in the sensing chamber, e.g., a reagent capable of undergoing a redox reaction with an analyte or a reaction product of the analyte. The chemical can be printed onto at least one wall of the sensing chamber, or contained in or on a support included in the sensing chamber. At least one of the sheet, thin layers, or covering layers can include, for example, polyethylene terephthalate. The second electrode layer can be mounted in opposing relationship a distance of less than 200 microns from the first electrode layer.

DETAILED DESCRIPTION OF THE PREFERRED EMBODIMENT

Figure 1:
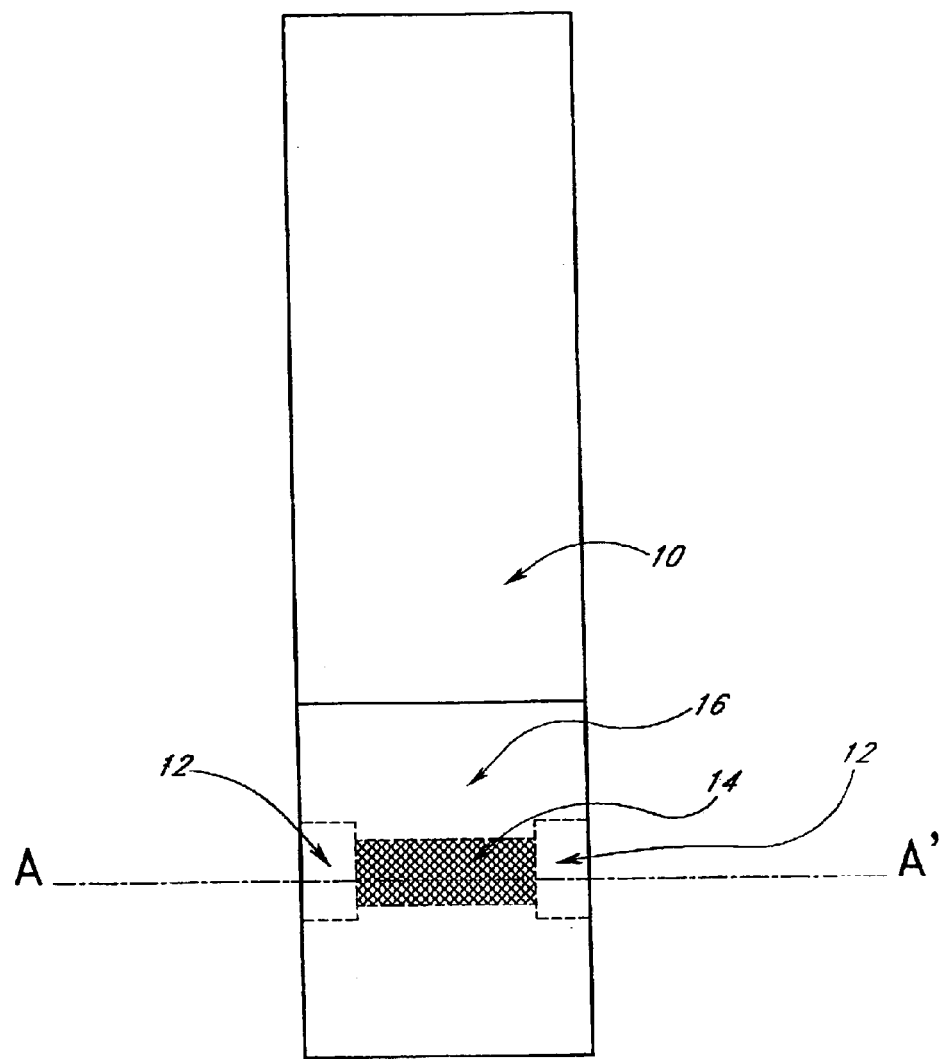
FIG. 1 provides a top view of the sampling device illustrating an arrangement of the pre-chamber and sensing chamber. In the illustrated embodiment, the device has two pre-chambers and one sensing chamber.

The following description and examples illustrate various embodiments of the present invention in detail. Those of skill in the art will recognize that there are numerous variations and modifications of this invention that are encompassed by its scope. Accordingly, the description of a preferred embodiment should not be deemed to limit the scope of the present invention. Methods and devices for sampling fluid samples are discussed further in copending U.S. patent application Ser. No. 09/536,235, filed on Mar. 27, 2000, now U.S. Pat. No. 6,612,111, entitled "METHOD AND DEVICE FOR SAMPLING AND ANALYZING INTERSTITIAL FLUID AND WHOLE BLOOD SAMPLES," which is incorporated herein by reference in its entirety.

The current invention provides a device 10, and a method for making and using the device 10, for ensuring that a capillary or wicking fill device 10 is fully filled. In particular this invention is directed to, but not limited to, use with capillary or wicking action filled electrochemical sensors.

The device 10 consists of a pre-chamber 12, which fills by capillary action or wicking action, which is in fluid communication with a sensing chamber 14, which also fills by capillary or wicking action. Reliable and substantially complete filling of the sensing chamber 14 is a primary object of the present invention.

The pre-chamber 12 has an interior surface and a volume, and is capable of exerting a first capillary force. The interior surface of the pre-chamber 12 comprises first and second pre-chamber walls 20 spaced apart at a first distance to define the pre-chamber height. The sensing chamber 14 also has an interior surface and a volume, and is capable of exerting a second capillary force different from that of the pre-chamber 12. The interior surface of the sensing chamber 14 comprises a first and a second sensing chamber wall 22 spaced apart at a second distance to define the height of the sensing chamber 14.

The difference between the capillary force exerted by the pre-chamber 12 and the sensing chamber 14 causes the flow of fluid from the pre-chamber 12 to the sensing chamber 14, so as to substantially fill the sensing chamber 14. To ensure that the sensing chamber 14 is substantially filled, the pre-chamber 12 is of such a volume that when full it contains at least as much or more sample than is needed to fill the sensing chamber 14. In a preferred embodiment, the layers 18 within the sensing chamber serve to define the sensing chamber 14. The layers 18 are spaced apart by a spacer layer (not shown in FIG. 1 or 2), wherein an aperture in the spacer layer defines the height of the sensing chamber 14. The pre-chamber 12 has end walls formed by layers 16. In this embodiment, the pre-chamber layers 16 are adhered or otherwise attached to the outer surfaces of the sensing chamber layers 18 in a suitable manner, such as by an adhesive.

Figure 2:
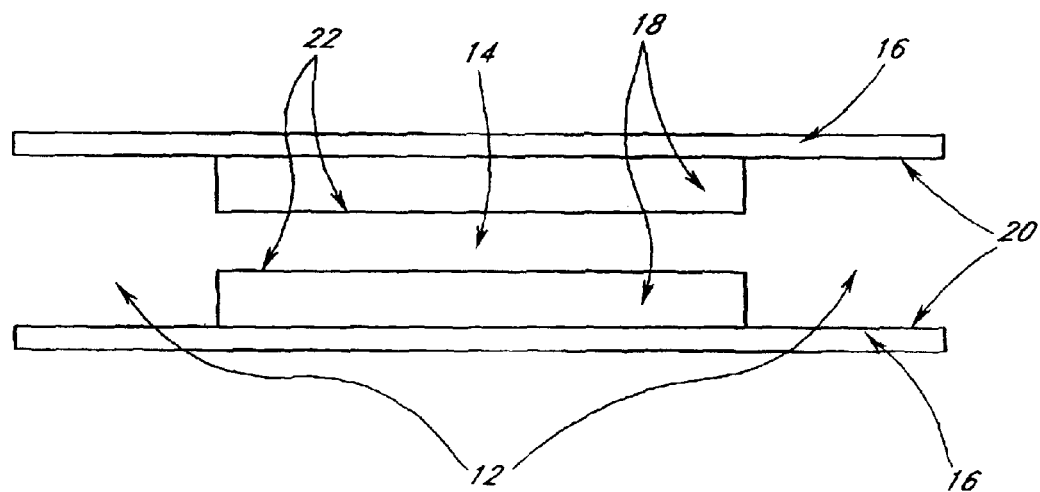
FIG. 2 provides a cross section of the device along line A–A' of FIG. 1.

In a preferred embodiment, a single pre-chamber 12 can be used. Alternatively, two pre-chambers 12 placed on opposite sides of the sensing chamber 14 chamber can be used, as illustrated in FIGS. 1 and 2. In such an embodiment, the device can be filled from both or either of the right and left sides of the device 10.

In use, a sample is introduced into the pre-chamber 12 through a port on a side of the pre-chamber 12 that is substantially opposite to the boundary between the pre-chamber 12 and the sensing chamber 14. Sample is drawn into the pre-chamber 12 and fills across the pre-chamber 12 from the sampling port side to the sensing chamber 14 opening side, until eventually sufficient sample has been introduced into the pre-chamber 12 that it begins to fill the sensing chamber 14. At this point, an optional detector detects that the sensing chamber 14 has begun to fill and indicates this to the user. Since by this time the pre-chamber 12 is fully filled with sample, there is sufficient total sample in the pre-chamber 12 to ensure that the sensing chamber 14 can be filled completely.

The stronger capillary or wicking force of the sensing chamber 14 as compared to that of the pre-chamber 12 ensures that once the sensing chamber 14 begins to fill, if no additional sample is added to the pre-chamber 12, then the sensing chamber 14 is capable of at least partially drawing the sample from the pre-chamber 12 to complete the filling of the sensing chamber 14. If filling of the pre-chamber 12 is interrupted prior to being fully filled, the detector is not triggered and the user knows that insufficient sample is present in the sensing chamber. Extra sample can then be added until the detector is triggered.

In a preferred embodiment of the present invention, the capillary force is made stronger in the sensing chamber 14 than the pre-chamber 12 by suitably treating the walls of the two chambers 12, 14 such that the energy liberated when the sample wets the walls of the sensing chamber 14 is greater than the energy needed to de-wet the walls of the first chamber 12. The surface treatment can be applied to either chamber, or both chambers, and can comprise any suitable hydrophilic or hydrophobic substance. For example, suitable substances include surfactants, block copolymers, hygroscopic compounds, or other substances that ionize or otherwise react with or dissolve in the sample. If both chambers 12, 14 are treated, the substance used to treat a given chamber 12, 14 can be the same as or different from that used to treat the other chamber 12, 14, so long as the aggregate capillary forces of the two chambers are different.

In another preferred embodiment, mesh is used to draw the sample into the chambers 12, 14, with a finer mesh in the sensing chamber 14 than the pre-chamber 12, so that the sample can be drawn into the sensing chamber 14 and empty the pre-chamber 12. In an alternative embodiment, the mesh in the sensing chamber 14, is not finer than the mesh in the pre-chamber, but instead contributes to a higher total capillary force within the sensing chamber by having a more negative energy of interaction with the wetting liquid than the mesh used in the pre-chamber 12. The energy of interaction of the mesh can be modified through the use of a surface treatment as described above. Alternatively, a fibrous filling material, a porous material, or a powder could be used to draw sample into the chambers 12, 14. Either or both of the chambers 12, 14 can contain a capillarity enhancer, such as, for example, a mesh, a fibrous filling material or a porous material. Such capillarity enhancers can be either soluble or insoluble in the sample. If both chambers 12, 14 contain a capillarity enhancer, such enhancer can be the same in both chambers or it can be different in each chamber, provided a differential in capillary force exists between the pre-chamber 12 and sensing chamber 14. Alternatively, various combinations of different meshes, different fibrous materials, and different porous materials are contemplated. Suitable mesh materials include, for example, polyolefin, polyester, nylon, cellulose, or meshes woven of fibrous materials. Suitable fibrous materials include, for example, nonwoven or melt blown materials, including polyolefin, polyester, nylon, cellulose, polystyrene, polycarbonate, polysulfone. Suitable porous materials include, for example, sintered powders or macroporous membranes such as those of polysulfone, polyvinylidenedifluoride, nylon, cellulose acetate, polymethacrylate, and polyacrylate. Suitable powders include microcrystalline cellulose, soluble or insoluble salts, and soluble powders such as sucrose.

In another preferred embodiment, the pre-chamber 12 has a larger height than the height of the sensing chamber 14, such that the capillary force drawing liquid into the sensing chamber 14 is greater than the force holding liquid in the pre-chamber 12. Here, the height of the capillary chamber typically refers to its smallest internal dimension. Alternatively, the surface roughness of the sensing chamber 14 can be made greater than the surface roughness of the pre-chamber chamber 12, such as, for example, by etching ridges or striations into the walls of the sensing chamber, or by designing the physical dimensions of the sensing chamber accordingly, such that the greater surface area of the sensing chamber provides a greater capillary force. Surface roughness is defined herein as the actual surface area divided by the geometric surface area.

In a particularly preferred embodiment of the present invention, capillary fill sensor strips 10 of the type disclosed in PCT/AU96/00724 are fabricated, and a section of the strip 10 which overlaps the sensing chamber 14 and intersects at least one edge of the strip 10 is removed. The notch disclosed in PCT/AU96/00724 is an example of such a region. Tape or other suitable layers 16 are then overlaid and sealed to both faces of the strip 10 so as to entirely cover the removed region. By this method a pre-chamber 12 is formed with an aperture or port opening to the edge of the strip 10 and an aperture or port opening to the sensing chamber 14 (which in this case is the sensing chamber 14 referred to above).

In this embodiment, the height of the pre-chamber 12 is that of the three laminate layers described in PCT/AU96/00724. The height of the sensing chamber 14 is the thickness of the separating layer between the two electrode layers, which is smaller than the height of the pre-chamber 12. The capillary force drawing sample into the sensing chamber 14 can therefore be stronger than the force holding the sample in the pre-chamber 12, such that the sensing chamber 14 fills and, if necessary, empties the pre-chamber 12 in the process. Emptying the pre-chamber 12 to at least some extent is necessary if the sample source is withdrawn from the pre-chamber 12 filling port during the filling of the sensing chamber 14.

In a preferred embodiment, the function of the detector is based on a change in voltage or current flowing between the sensing electrodes, which can comprise a noble metal, e.g., palladium, platinum or silver. The optimal distance between the electrodes is a function of the reagents and conditions used, the analyte of interest, the total volume of the cell, and the like. In one embodiment, the electrodes are spaced apart at a distance of about 400 to 600 microns. In a preferred embodiment, the electrodes are about 300 microns apart. In a more preferred embodiment, the electrodes are spaced apart by a distance of 200 microns, or less. Various most preferred embodiments have electrodes spaced about 40, 80, 120, or 160 microns. The cell can contain one or more chemicals, e.g., a reagent capable of undergoing a redox reaction with the analyte or a reaction product of the analyte, the redox reaction producing a voltage or current indicative of the concentration of the analyte. At this point the meter used in conjunction with the test strip can optionally indicate visually or aurally that sufficient sample has been introduced. Other detectors useful with the current invention can function based on the attenuation or change of position of a transmitted light beam, the change in reflectance of a reflected light beam or any other features that are capable of detection when the sample enters the sensing chamber 14.

In a preferred embodiment, the device 10 can be used as a glucose monitoring test strip, with the fluid sample being blood or interstitial fluid. Other biological fluids that can be sampled using the device 10 include other animal body fluids, such as, for example, tears, expectorate, saliva, urine, semen, vomitus, and sputum. Alternatively, the biological fluid can comprise a plant extract, nectar, sap, or fruit or vegetable juice. Food products, e.g., beverages, can be tested. Non-biological fluids can be tested as well, e.g., process water, drinking water, or water-based solutions.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A device for sampling a fluid, comprising a pre-chamber having an interior surface and a first volume, the pre-chamber being capable of exerting a first capillary force, the device further comprising a sensing chamber in fluid communication with the pre-chamber, the sensing chamber having an interior surface and a second volume, the sensing chamber being capable of exerting a second capillary force, wherein the first volume is not less than the second volume, and wherein a differential exists between the capillary forces, the differential being sufficient to cause flow of fluid from the pre-chamber to substantially fill the sensing chamber.

2. The device of claim 1, wherein the interior surface of the pre-chamber comprises at least first and second pre-chamber walls spaced apart at a first distance to define a pre-chamber height, and wherein the interior surface of the sensing chamber comprises at least first and second sensing chamber walls spaced apart at a second distance to define a sensing chamber height, wherein the height of the sensing chamber is less than the height of the pre-chamber, and wherein the differential capillary force derives at least in part from a difference between the pre-chamber height and the sensing chamber height.

3. The device of claim 1, the interior surface of the pre-chamber having a first surface roughness, a first actual surface area, and a first geometric surface area, and the interior surface of the sensing chamber having a second surface roughness, a second actual surface area, and a second geometric surface area, wherein the second surface roughness is greater than the first surface roughness, and wherein the differential capillary force derives from a difference between the second surface roughness and the first surface roughness, and wherein the surface roughness is defined as the actual surface area divided by the geometric surface-area.

4. The device of claim 1, the interior surface of at least the pre-chamber or the sensing chamber comprising a surface treatment, wherein the differential capillary force derives from the surface treatment.

5. The device of claim 4, wherein the surface treatment comprises a hydrophilic substance.

6. The device of claim 4, wherein the surface treatment comprises a hydrophobic substance.

7. The device of claim 4, wherein the surface treatment comprises a substance selected from the group consisting of a surfactant, a block copolymer, a hygroscopic compound, an ionizable substance, and mixtures thereof.

8. The device of claim 4, wherein the interior surface of the pre-chamber comprises a first surface treatment and the interior surface of the sensing the chamber comprises a second surface treatment.

9. The device of claim 1, further comprising a porous material, wherein the porous material contributes to the capillary force of at least one of the pre-chamber and the sensing chamber.

10. The device of claim 9, wherein both the pre-chamber and the sensing chamber comprise a porous material.

11. The device of claim 9, wherein the porous material is selected from the group consisting of a sintered powder and a macroporous membrane.

12. The device of claim 9, wherein the porous material comprises a macroporous membrane comprising a polymeric material, wherein the polymeric material is selected from the group consisting of polysulfone, polyvinylidenedifluoride, nylon, cellulose acetate, polymethacrylate, polyacrylate, and mixtures thereof.

13. The device of claim 1, further comprising a powder, wherein the powder contributes to the capillary force of at least one of the pre-chamber and the sensing chamber.

14. The device of claim 13, wherein both the pre-chamber and the sensing chamber comprise a powder.

15. The device of claim 13, wherein the powder is insoluble in the sample.

16. The device of claim 13, wherein the powder is soluble in the sample.

17. The device of claim 13, wherein the powder comprises a material selected from the group consisting of microcrystalline cellulose, soluble salts, insoluble salts, and sucrose.

18. The device of claim 1, wherein the pre-chamber and the sensing chamber comprise two or more materials, which can be the same or different, selected from the group consisting of a mesh material, a fibrous filling material, a porous material, and a powder.

19. The device of claim 1, wherein the sensing chamber comprises electrodes capable of use in an electrochemical cell.

20. The device of claim 19, wherein the electrodes are spaced apart by 600 microns or less.

21. The device of claim 19, wherein the electrodes are spaced apart by 400 microns or less.

22. The device of claim 19, wherein the electrodes are spaced apart by 200 microns or less.

23. The device of claim 1, further comprising a detector capable of detecting a condition wherein the pre-chamber contains a volume of fluid sufficient to substantially fill the sensing chamber.

24. A glucose monitoring test strip comprising the device of claim 1.

25. A device for sampling a fluid, comprising a pre-chamber having an interior surface and a first volume, the pre-chamber being capable of exerting a first capillary force, the device further comprising a sensing chamber in fluid communication with the pre-chamber, the sensing chamber having an interior surface and a second volume, the sensing chamber being capable of exerting a second capillary force, wherein the first volume is not less than the second volume, and wherein a differential exists between the capillary forces, the differential being sufficient to cause flow of fluid from the pre-chamber to substantially fill the sensing chamber, and wherein the device further comprises a mesh material and the mesh material contributes to the capillary force of at least one of the pre-chamber and the sensing chamber.

26. The device of claim 25, wherein both the pre-chamber and the sensing chamber comprise a mesh material.

27. A device for sampling a fluid, comprising a pre-chamber having an interior surface and a first volume, the pre-chamber being capable of exerting a first capillary force, the device further comprising a sensing chamber in fluid communication with the pre-chamber, the sensing chamber having an interior surface and a second volume, the sensing chamber being capable of exerting a second capillary force, wherein the first volume is not less than the second volume, and wherein a differential exists between the capillary forces, the differential being sufficient to cause flow of fluid from the pre-chamber to substantially fill the sensing chamber, and wherein the device further comprises a fibrous filling material that contributes to the capillary force of at least one of the pre-chamber and the sensing chamber.

28. The device of claim 27, wherein both the pre-chamber and the sensing chamber comprise a fibrous filling material.

29. The device of claim 27, wherein the fibrous filling material comprises a material selected from the group consisting of polyolefin, polyester, nylon, cellulose, polystyrene, polycarbonate, and polysulfone.

30. The device of claim 27, wherein the fibrous filling material comprises a nonwoven or melt blown polymer.

* * * * *